US010478068B2

(12) United States Patent
Zhang et al.

(10) Patent No.: US 10,478,068 B2
(45) Date of Patent: Nov. 19, 2019

(54) CAMERA DEVICE HAVING A PARABOLIC MIRROR SET BETWEEN DUAL CAMERAS AND METHOD FOR SHOOTING LIGHT HAVING AT LEAST TWO WAVELENGTH BANDS

(71) Applicants: Yupeng Zhang, Beijing (CN); Hong Yi, Beijing (CN); Weitao Gong, Beijing (CN); Haihua Yu, Beijing (CN); Wei Wang, Beijing (CN)

(72) Inventors: Yupeng Zhang, Beijing (CN); Hong Yi, Beijing (CN); Weitao Gong, Beijing (CN); Haihua Yu, Beijing (CN); Wei Wang, Beijing (CN)

(73) Assignee: Ricoh Company, Ltd., Tokyo (JP)

( * ) Notice: Subject to any disclaimer, the term of this patent is extended or adjusted under 35 U.S.C. 154(b) by 183 days.

(21) Appl. No.: 15/869,710

(22) Filed: Jan. 12, 2018

(65) Prior Publication Data

US 2018/0249910 A1 Sep. 6, 2018

(30) Foreign Application Priority Data

Mar. 3, 2017 (CN) .......................... 2017 1 0123684

(51) Int. Cl.
*A61B 5/00* (2006.01)
*G01T 1/16* (2006.01)
*A61B 6/00* (2006.01)
*G01T 1/29* (2006.01)

(52) U.S. Cl.
CPC .......... *A61B 5/0035* (2013.01); *A61B 5/0046* (2013.01); *A61B 5/0082* (2013.01); *A61B 6/5247* (2013.01); *G01T 1/1603* (2013.01); *G01T 1/295* (2013.01)

(58) Field of Classification Search
CPC ... A61B 5/0035; A61B 5/0046; A61B 5/0082; A61B 5/1176; A61B 6/5247; G01T 1/1603; G01T 1/295; H04N 5/332; G02B 27/1006
USPC ..................................... 250/216, 239, 208.1
See application file for complete search history.

(56) References Cited

U.S. PATENT DOCUMENTS 10,335,896 B2 * 7/2019 Berg

* cited by examiner

*Primary Examiner* — Que Tan Le
(74) *Attorney, Agent, or Firm* — IPUSA, PLLC

(57) ABSTRACT

Camera device and method for shooting light having at least two wavelength bands are disclosed. The camera device includes a first camera containing a first lens for receiving light having a first wavelength band; a second camera including a second lens for receiving light having a second wavelength band which is different from the first wavelength band, the second lens being disposed facing the first lens of the first camera; and a parabolic mirror set between the first camera and the second camera, able to let the light having the first wavelength band penetrate therethrough, and at the same time, reflect the light having the second wavelength band. The first camera is a non-fisheye camera. The first lens is a non-fisheye lens. The second camera and the parabolic mirror form a catadioptric camera. The aperture stop of the non-fisheye lens coincides with the focal point of the parabolic mirror.

10 Claims, 7 Drawing Sheets

$\theta \neq \gamma_1; \theta = \gamma_2$

CAMERA DEVICE HAVING A PARABOLIC MIRROR SET BETWEEN DUAL CAMERAS AND METHOD FOR SHOOTING LIGHT HAVING AT LEAST TWO WAVELENGTH BANDS

BACKGROUND OF THE DISCLOSURE

1. Field of the Disclosure

The present disclosure relates to the field of multimodal imaging, and more particularly relates to a camera device for conducting a multimodal imaging process and a method for shooting light having at least two wavelength bands.

2. Description of the Related Art

A multimodal imaging system is a kind of camera system by which it is possible to take visible and invisible light (e.g., infrared light) pictures. It has been widely applied in many fields such as human face recognition, pedestrian detection, monitoring, and the like, and its purpose is to improve the ability of detection, tracking, and recognition in a case of bad weather, for example, low light, fog, rain, or snow. In terms of object detection, visible and invisible light is mutually complementary. For instance, when recognizing a human face, long-wave infrared (far-infrared) light cannot penetrate through a pair of glasses, but visible light may penetrate through the pair of glasses. This may result in loss of some eye features in the captured far-infrared light based image; however, these types of eye features may be detected in the taken visible light based image. On the other hand, when driving at night, a far-infrared light camera is easy to detect a pedestrian, but a visible light camera is very difficult to do that.

In conventional techniques, there are a lot of approaches able to achieve multimodal imaging in a multimodal camera. Generally speaking, the following two types of approaches are well used, namely, (1) disposing a visible light camera and an infrared light camera in parallel, as shown in FIG. 1 that illustrates the basic structure of a conventional multimodal camera; and (2) letting the optical axes of a visible light camera and an infrared light camera be perpendicular to each other and setting a spectroscope (e.g., a hot or cold mirror) therebetween, as presented in FIG. 2 which illustrates the basic structure of another conventional multimodal camera.

In the first type of approach, the optical axes of the visible light camera and the infrared light camera are parallel to each other, so that the view fields of these two cameras are different, thereby generating parallax between the visible and infrared light images captured. As such, when using this kind of multimodal camera to conduct detection and tracking, it is necessary to first carry out correction with respect to the visible light camera and the infrared light camera so as to remove the influence due to the parallax. This may undoubtedly increase the amount of calculation.

Additionally, in the second type of approach, visible light (or infrared light) penetrates through the spectroscope while the infrared light (or the visible light) is reflected by the same spectroscope. Since the visible light camera and the infrared light camera are essentially coaxial, no parallax occurs between these two cameras. However, when this kind of multimodal camera is adopted, because its view angle (view field) must be smaller than the size of the spectroscope, the corresponding system is relatively heavy and hardly miniaturized.

SUMMARY OF THE DISCLOSURE

In light of the above, the present disclosure provides a camera device and a method for shooting light having at least two wavelength bands.

According to a first aspect of the present disclosure, a camera device is provided which includes a first camera containing a first lens for receiving light having a first wavelength band; a second camera having a second lens for receiving light having a second wavelength band different from the first wavelength band, the second lens being disposed facing the first lens of the first camera; and a parabolic mirror disposed between the first lens and the second lens, able to let the light having the first wavelength band penetrate therethrough, and at the same time, reflect the light having the second wavelength band.

The first camera is a non-fisheye camera. The first lens of the first camera is a non-fisheye lens. The second camera and the parabolic mirror form a catadioptric camera. The aperture stop of the non-fisheye lens coincides with the focal point of the parabolic mirror.

According to a second aspect of the present disclosure, a method of shooting light having at least two wavelength bands is provided which includes steps of letting incident light enter a parabolic mirror set between a first lens and a second lens; causing, by the parabolic mirror, light having a first wavelength band to penetrate through the parabolic mirror itself, and at the same time, reflecting light having a second wavelength band by the parabolic mirror; receiving the light having the first wavelength band by a first camera containing the first lens able to receive the light having the first wavelength band; receiving the light having the second wavelength band different from the second wavelength band by a second camera having the second lens able to receive the light having the second wavelength band, the second lens being disposed facing the first lens of the first camera; and performing photoelectric conversion on the light having the first wavelength band and the light having the second wavelength band so as to form two images, respectively.

The first camera is a non-fisheye camera. The first lens of the first camera is a non-fisheye lens. The second camera and the parabolic mirror form a catadioptric camera. The aperture stop of the non-fisheye lens coincides with the focal point of the parabolic mirror.

Therefore, in the camera device and the method, by letting the aperture stop of the first camera coincide with the focal point of the parabolic mirror, it is possible to achieve the same view field. Furthermore, because the parabolic mirror is set between the first camera and the second camera whose lenses are disposed facing each other, the miniaturization of the relating system may also be realized.

DETAILED DESCRIPTION OF THE PREFERRED EMBODIMENTS

Figure 1:
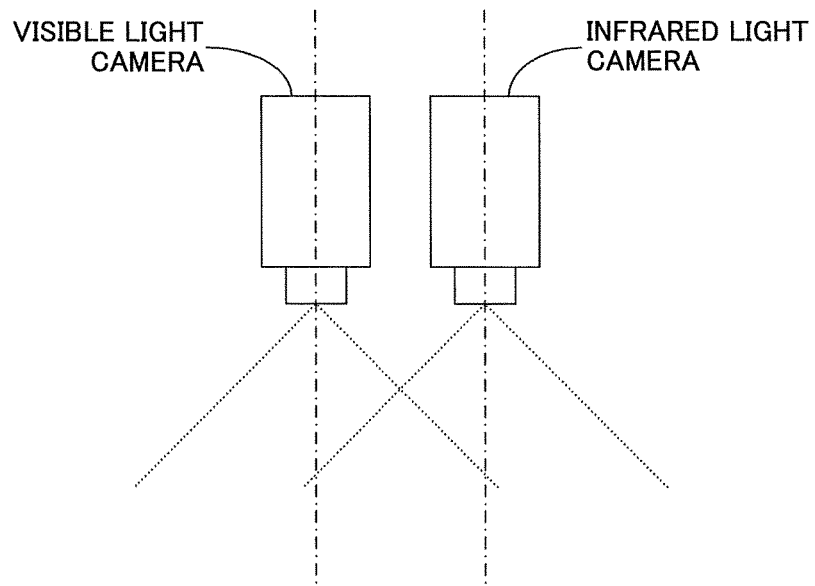
FIG. 1 illustrates the basic structure of a conventional multimodal camera.

In order to let a person skilled in the art better understand the present disclosure, hereinafter, the embodiments of the present disclosure will be concretely described by referring to the drawings. However, it should be noted that the same symbols, which are in the specification and the drawings, stand for constructional elements having basically the same function and structure, and the repetition of the explanations to the constructional elements is omitted.

First Embodiment

In this embodiment, a camera device for conducting a multimodal imaging process is provided.

Figure 3:
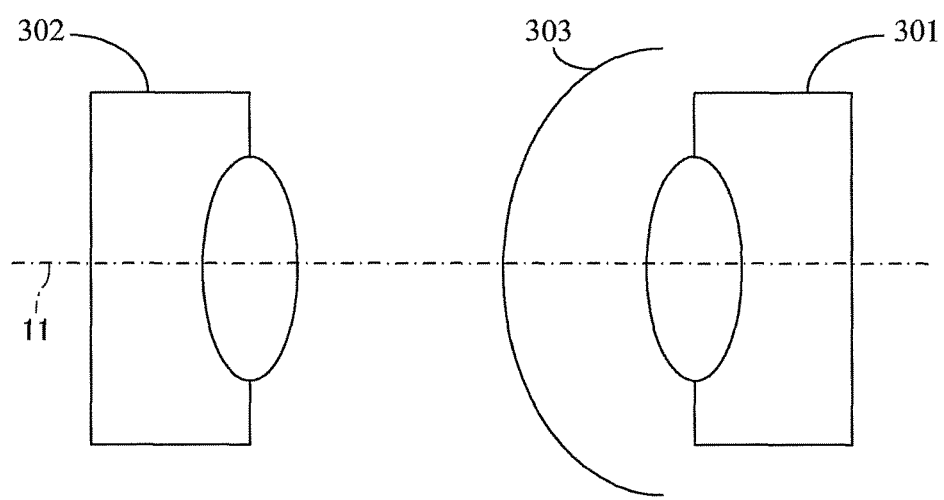
FIG. 3 illustrates the fundamental structure of a camera device according to a first embodiment of the present disclosure.

FIG. 3 illustrates the fundamental structure of a camera device 300 according to this embodiment.

As shown in FIG. 3, the camera device 300 contains a first camera 301, a second camera 302, and a parabolic mirror 303.

Figure 2:
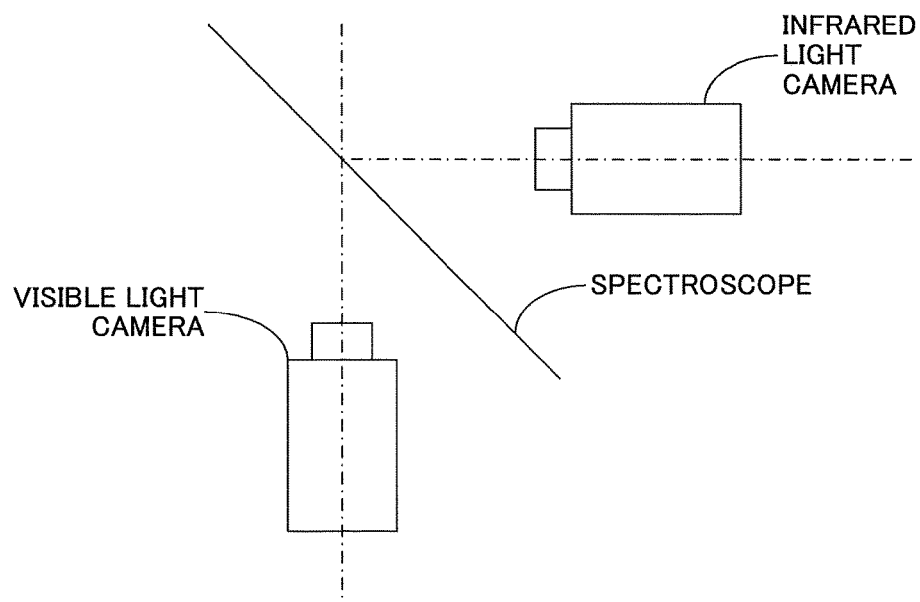
FIG. 2 illustrates the basic structure of another conventional multimodal camera.

The first camera 301 includes a first lens for receiving light having a first wavelength band. The second camera 302 contains a second lens for receiving light having a second wavelength band which is different from the first wavelength band. Unlike the basic structures of the conventional multimodal cameras as presented in FIGS. 1 and 2, in the camera device 300, the first lens of the first camera 301 is disposed facing the second lens of the second camera 302. Moreover, the parabolic mirror 303 is provided between the first lens and the second lens, and may let the light having the first wavelength band penetrate and reflect the light having the second wavelength band at the same time.

In an example, the material of the parabolic mirror 303 may be germanium (Ge), zinc sulfide, etc. Aside from this, a plating film may be provided on the surface of the parabolic mirror 303. In this way, it is possible to achieve a two-way or half mirror which may cause the light in the first wavelength band to penetrate and simultaneously reflect the light in the second wavelength band. The description about the manufacturing process of the parabolic mirror 303 is omitted for the sake of convenience because it is not closely related to the embodiments of the present disclosure.

In another example, the parabolic mirror 303 is also able to let light having any wavelength band penetrate and reflect the same light in the meantime. In this case, the receiving abilities of the first camera 301 and the second camera 302 are different. That is, the first camera 301 may receive only the light having the first wavelength band, and the second camera 302 may receive only the light having the second wavelength band. The manufacturing process of this kind of parabolic mirror is relatively simple, and its description is also omitted for the same reason.

Here it should be noted that the structure of the parabolic mirror 303 is not limited to the above two examples. In other words, any type of parabolic mirror, by which only the light having the first wavelength band may arrive at the first camera 301 and only the light having the second wavelength band may enter the second camera 302, may serve as the parabolic mirror 303.

Figure 4A:
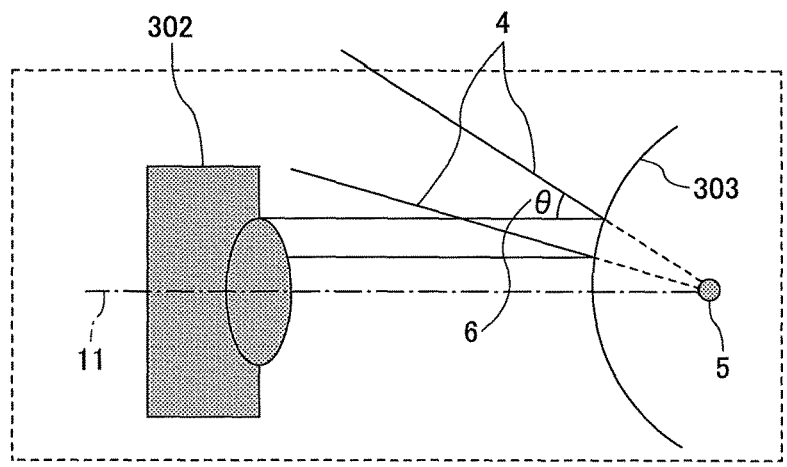
FIG. 4A illustrates an optical path of a catadioptric camera.

Additionally, in the camera device 300, the second camera 302 and the parabolic mirror 303 form a catadioptric camera, as shown in FIG. 4A which illustrates an optical path of a catadioptric camera. As presented in this drawing, due to the optical characteristics of the parabolic mirror 303, the incident light 4, whose extension straight lines pass through the focal point 5 of the parabolic mirror 303, is reflected by the parabolic mirror 303, so that the incident light 4 may become light parallel to the optical axis 11 of the second camera 302, which enters the second camera 302. It should be noted that the optical axis 11 of the second camera 302 is also the optical axes of the catadioptric camera and the first camera 301.

Hereinafter, the concept of half view angle is introduced. In the catadioptric camera indicated in FIG. 4A, the half view angle 6 ($\theta$) is generated by the incident light 4 and the reflected light.

Figure 4B:
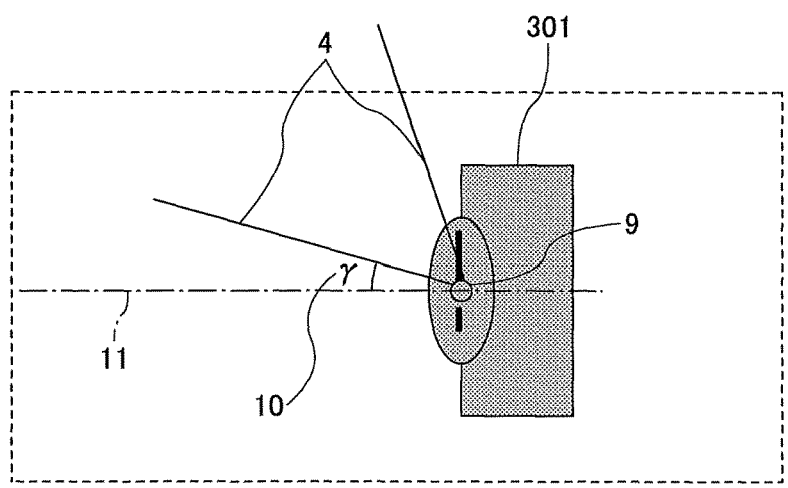
FIG. 4B illustrates an optical path of a non-fisheye camera.

FIG. 4B individually illustrates the first camera 301 which is a non-fisheye camera.

It should be noted that for the sake of the follow-on calculation, as presented in FIG. 4B, the incident light 4 entering the aperture stop 9 of the first camera 301 (here the aperture stop 9 is also the aperture stop of the first lens) cannot change its propagation direction, i.e., cannot be bent. As such, in the embodiments of the present disclosure, the first camera 301 must be a non-fisheye camera, and the first lens must be a non-fisheye lens. In the non-fisheye camera shown in this drawing, the half view angle 10 ($\gamma$) is formed by the incident light 4 penetrating through the parabolic mirror 303 and the optical axis 11.

In a case where the incident light 4 shown in FIG. 4A and the incident light 4 indicated in FIG. 4B come from the same object point, if the half view angle 6 ($\theta$) in the catadioptric camera presented in FIG. 4A is equal to the half view angle 10 ($\gamma$) in the non-fisheye camera shown in FIG. 4B, then it may be regarded that the field angels of these two cameras are the same, i.e., there is no parallax between these two cameras.

Figure 5A:
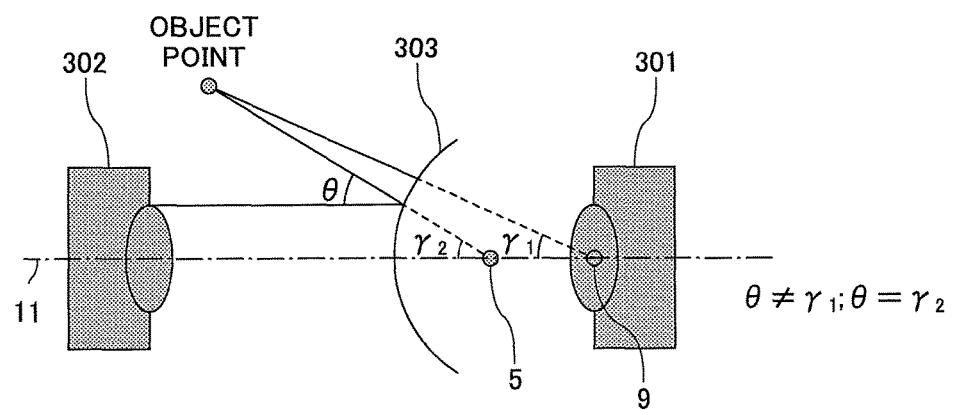
FIG. 5A illustrates the camera device under different view angles, according to the first embodiment of the present disclosure.

FIG. 5A illustrates the camera device 300 under different view angles.

Figure 5B:
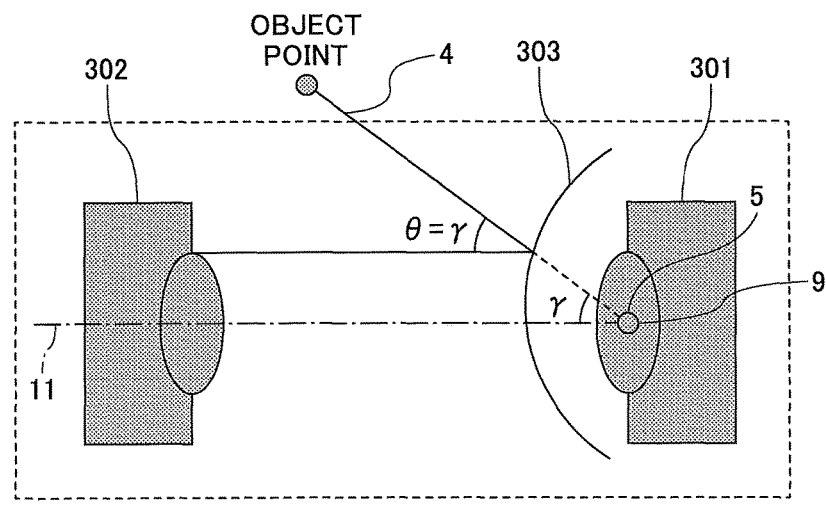
FIG. 5B illustrated the camera device under the same view angle, according to the first embodiment of the present disclosure.

FIG. 5B illustrates the camera device 300 under the same view angle.

As indicated in FIG. 5A, the half view angle of the second camera 302 with respect to the object point is $\theta$. If the aperture stop 9 of the first camera 301 does not coincide with the focal point 5 of the parabolic mirror 303, then the half view angle of the first camera 301 in regard to the same object point is $\gamma_1$. According to the knowledge of geometry, it is obvious that in FIG. 5A, $\theta=\gamma_2$, and $\gamma_1 \neq \gamma_2$, so $\theta \neq \gamma_1$. In other words, the view angles of the first camera 301 and the second camera 302 are different, thereby resulting in parallax between these two cameras.

On the other hand, as presented in FIG. 5B, the aperture stop 9 of the first camera 301 and the focal point 5 of the parabolic mirror 303 overlap. As such, the half view angle γ of the first camera 301 is equal to the half view angle θ of the second camera 302; that is, there is no parallax between these two cameras.

As a result, in the camera device 300, by disposing the first camera 301 and the second camera 302 facing each other, and utilizing the parabolic mirror 303 to adjust the view angles of these two cameras to be the same, no parallax occurs between these two cameras. In addition, this kind of design may reduce the whole size of the camera device 300, so it is of benefit to achieving the miniaturization of the relating system.

In an example, in the catadioptric camera, the incident light 4 is reflected by the parabolic mirror 3, and then, enters a sensor of the second camera 302 in parallel with the optical axis 11. The aperture stop of the second camera 302 is located at the posterior focus of the second lens therein. That is, the catadioptric camera is the so-called "object side telecentric optical system".

In order to ensure that the first camera 301 and the second camera 302 have the same view angle, the positional relationship between the first camera 301 and the parabolic mirror 303 is fixed. However, the distance from the second camera 302 to the parabolic mirror 303 may be changed. If the distance between the second camera 302 and the parabolic mirror 303 is relatively small, then the blind area of the second camera 302 is relatively large. On the contrary, if the distance between the second camera 302 and the parabolic mirror 303 is relatively large, then the blind area of the second camera 302 is relatively small. When adjusting the distance from the second camera 302 to the parabolic mirror 303 as needed, the so-called "object side telecentric optical system" may guarantee that there is not a significant difference between the images captured by the second camera 302 before and after adjustment (for example, the magnification rate is almost the same).

Hereinafter, some examples of choosing the first wavelength band and the second wavelength band are provided.

In a first example, it is assumed that the first wavelength band is a visible light wavelength band, and the second wavelength band is an invisible light wavelength band. Hence, as shown in FIG. 3, by utilizing the parabolic mirror 303, it is possible to let light having a visible light wavelength band (i.e., the first wavelength band) penetrate so as to arrive at the first lens in the first camera 301, and reflect light having a far-infrared light wavelength band (i.e., the second wavelength band) so as to cause it to enter the second lens in the second camera 302. In this way, these two types of light having the same view field and different wavelength bands may be shot by the first lens of the first camera 301 and the second lens of the second camera 302, respectively. In other words, if a lighting condition is good (e.g., in the day-time), it is possible to present a picture or video photographed based on the light having the visible light wavelength band received by the first lens in the first camera 301. Here it should be noted that in this case, although a picture or video taken according to the light having the far-infrared light wavelength band received from the second lens in the second camera 302 may also exist, it may not be presented, or may be output to a user after being processed. In addition, if the lighting condition is bad (e.g., in the night-time), it is possible to present a picture or video taken based on the light having the far-infrared light wavelength band received by the second lens in the second camera 302, so that an object imaged on the grounds of the far-infrared light may be captured. This may play a very important role in the fields of human being detection, security monitoring, and so on.

In a second example, it is supposed that the first wavelength band belongs to an invisible light wavelength band, and the second wavelength band belongs to a visible light wavelength band. Thus, as indicated in the FIG. 3, light in a far-infrared light wavelength band (i.e., an invisible light wavelength band) may penetrate through the parabolic mirror 303 so as to enter the first lens of the first camera 301, and light in a visible light wavelength band may be reflected by the parabolic mirror 303 so as to arrive at the second lens of the second camera 302. In this way, these two types of light having the same view angle and different wavelength bands may also be shot by the first lens of the first camera 301 and the second lens of the second camera 302, respectively.

Here it should be noted that one of the first camera 301 and the second camera 302 receiving the light having the invisible light wavelength band may be a thermal imaging camera, and the other camera receiving the light having the visible light wavelength band may be a charge-coupled device (CCD), complementary metal oxide semiconductor (CMOS) camera, etc.

Of course, the selection of the first wavelength band and the second wavelength band is not limited to the above examples. Generally speaking, the light in the first wavelength band may be visible light, and the light in the second wavelength band may be one of near-infrared light, short-wave infrared light, mid-wave infrared light, and long-wave infrared light. Alternatively, the light having the second wavelength band may be visible light, and the light having the first wavelength band may be one of near-infrared light, short-wave infrared light, mid-wave infrared light, and long-wave infrared light.

Furthermore, the light in the first wavelength band or the light in the second wavelength band may actually be light having any wavelength band, such as ultraviolet rays, light whose wavelength band is located within a range from a wavelength band to another wavelength band (e.g., from a red light wavelength band to a blue light wavelength band), or the like. However, an instrument shooting visible light, far-infrared light, mid-infrared light, or near-infrared light is well used generally, so, when taking advantage of this kind of instrument, it is not necessary to significantly modify its structure and configuration. That is, be means of this type of instrument, it is possible to more easily and efficiently achieve the technical solutions proposed in the embodiments of the present disclosure.

Moreover, as set forth above, in the camera device 300, a configuration, that the aperture stop 9 of the first cameras 301 is superimposed on the focal point of the parabolic mirror 303, is adopted so as to obtain the same view field. In order to realize the superposition of the aperture stop 9 of the first camera 301 and the focal point of the parabolic mirror 303, it is necessary to decide how to put the parabolic mirror 303 and the first camera 301 (i.e., a non-fisheye camera), namely, determine a distance from the vertex of the parabolic mirror 303 to the central position of the front end of the non-fisheye camera so as to dispose the non-fisheye camera and the parabolic mirror 303 on the basis of the distance.

Figure 6:
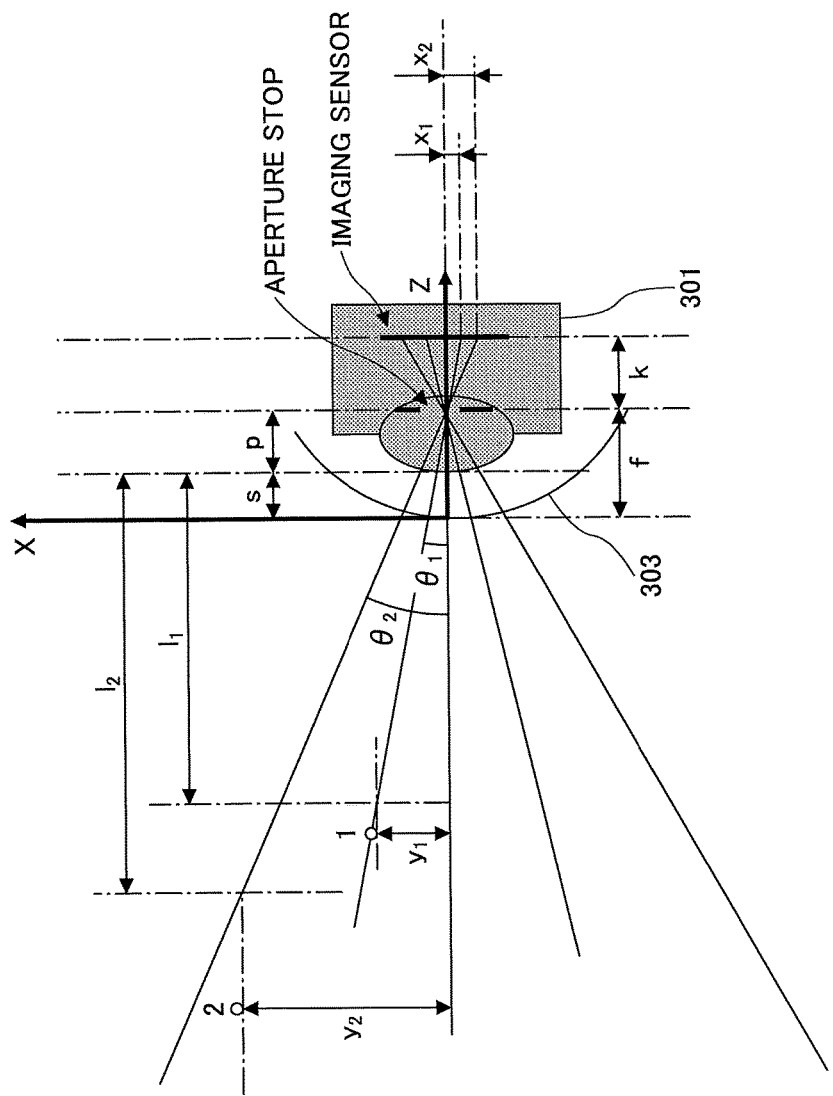
FIG. 6 illustrates a process of determining the positional relationship between a non-fisheye camera and a parabolic mirror.

In what follows, a process, of calculating the distance by way of a first processor (not shown in the drawings) which is included in the camera device 300, is given by referring to FIG. 6.

FIG. 6 illustrates how to determine the positional relationship between the non-fisheye camera (i.e., the first camera 301) and the parabolic mirror 303.

As indicated in FIG. 6, the aperture stop of the non-fisheye camera (i.e., the aperture stop of the non-fisheye lens in the non-fisheye camera) is located at the focal point of the parabolic mirror 303. In this drawing, s refers to the distance from the vertex of the parabolic mirror 303 to the central position of the front end of the non-fisheye camera, which is to be solved; f stands for the focal length of the parabolic mirror 303, which is known; $y_1$ and $y_2$ respectively denote the heights of first and second objects 1 and 2 corresponding to two real objects, which may be determined by way of measurement, i.e., are known; $x_1$ and $x_2$ respectively mean the heights of the images generated based on the first and second objects, which are known (e.g., the height of each image may be acquired by determining the number of pixels of the same image along its height direction, and then, converting the number of the pixels into the height of the same image on the ground of a predetermined proportional relationship between the size (i.e., the maximum longitudinal dimension) and the resolution (i.e., the maximum number of pixels in the longitudinal direction) of the related image sensor); $l_1$ is the distance between the first object 1 and the central point of the front end of the non-fisheye camera, which may be measured, i.e., is known; $l_2$ indicates the distance between the second object 2 and the central point of the front end of the non-fisheye camera, which may be determined by way of measurement, i.e., is also known; k is indicative of the distance between the related imaging unit in the non-fisheye camera and the aperture stop, which is unknown; and p represents the distance between the aperture stop and the central point of the front end of the non-fisheye camera, which is also unknown.

Thus, on the basis of the proportional relationship of similar triangles, it is possible to attain the following formula (1).

$$\begin{cases} \dfrac{p+l_1}{k} = \dfrac{y_1}{x_1} \\ \dfrac{p+l_2}{k} = \dfrac{y_2}{x_2} \end{cases} \quad (1)$$

Here, as described above, $x_1$, $y_1$, $x_2$, $y_2$, $l_1$, and $l_2$ are known, and p and k are unknown; as such, p and k may be solved.

And then, the distance s may be calculated by using the following formula (2).

$$s = f - p \quad (2)$$

Moreover, in FIG. 6, the half view angles corresponding to the objects points of the first and second objects 1 and 2 may be computed according to the following formulas (3) and (4).

$$\theta_1 = \arctan\left(\dfrac{y_1}{p+l_1}\right) \quad (3)$$

$$\theta_2 = \arctan\left(\dfrac{y_2}{p+l_2}\right) \quad (4)$$

It is obvious from the above that in order to procure the distance s between the vertex of the parabolic mirror 303 and the central point of the front end of the non-fisheye camera, the key is solving the distance p between the aperture stop of the non-fisheye lens in the non-fisheye camera and the central point of the front end of the non-fisheye camera. Additionally, the measurement for determining p is carried out with respect to only the non-fisheye camera. In other words, when measuring $x_1$, $y_1$, $x_2$, $y_2$, $l_1$, and $l_2$, it is not necessary to dispose the parabolic mirror 303. After acquiring the values of $x_1$, $y_1$, $x_2$, $y_2$, $l_1$, and $l_2$ by means of measurement and solving p, it is possible to attain the distance s. After that, the parabolic mirror 303 may be set on the basis of the distance s. In this way, it is possible to ensure that the aperture stop of the non-fisheye camera and the focal point of the parabolic mirror 303 overlap, and the view angles of the non-fisheye camera (i.e., the first camera 301) and the second camera 302 are the same.

Here it should be noted that in the camera device 300, the first camera 301 faces the second camera 302, so, when taking a picture, the image of the second camera 302 may exist in the image photographed by the first camera 301, and the image of the first camera 301 may also be present in the image photographed by the second camera 302. As such, preferably, the image of one of these two cameras is removed, which should not exist in the image taken by the other camera. For example, it is possible to delete this type of image by conducting post-processing. Alternatively, this kind of image may be eliminated by changing the hardware configuration of the camera device 300.

In the following, an example of removing, by modifying the hardware arrangement of the camera device 300, the image of one of the first camera 301 and the second camera 302, which is not necessary to the image taken by the other camera, is given.

Figure 7:
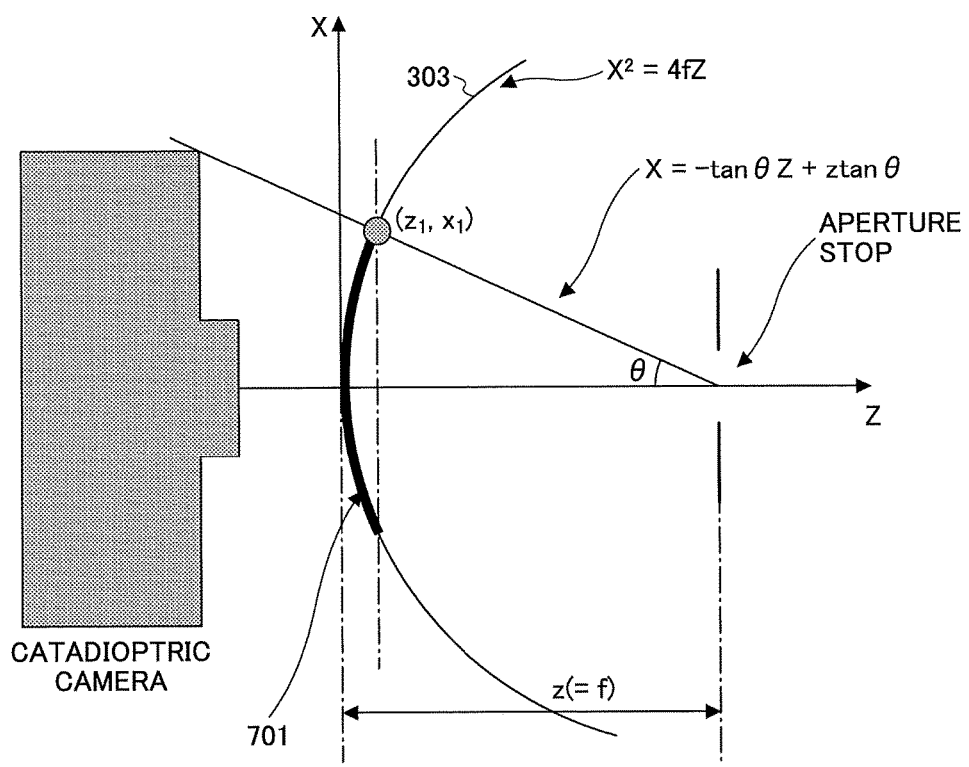
FIG. 7 illustrates a light barrier contained in a catadioptric camera.

FIG. 7 illustrates a catadioptric camera formed by the second camera 302 and the parabolic mirror 303, containing a light barrier 701.

As presented in FIG. 7, the camera device 300 further includes a light barrier 701 which is provided on a central part of the front surface of the parabolic mirror 303 for shading a part of the curved surface of the parabolic mirror 303 from light, so that the light may not be reflected by or penetrate through the part of the curved surface of the parabolic mirror 303 to enter the first camera 301 and the second camera 302. Here the light barrier 701 is a curved plate.

The size of the light barrier 701 cannot be too small; otherwise, it is impossible to completely avoid a circumstance where the image of one of the first camera 301 and the second camera 302 exists in the image taken by the other camera. On the other hand, the size of the light barrier 701 cannot be too large; otherwise, the light is blocked too much so that the view field of each of the first camera 301 and the second camera 302 is reduced. As a result, it is necessary to properly design the size of the light barrier 701.

In what follows, a process, of determining the size of the light barrier 701 by means of a second processor which is contained in the camera device 300, is introduced with reference to FIG. 7. Here the second processor and the first processor mentioned above may be the same processor.

As illustrated in FIG. 7, a two dimensional (X-Z) coordinate system is defined in which the origin is located at the vertex of the parabolic mirror 303; X axis is the common optical axis of the catadioptric camera and the first camera 301; X axis is perpendicular to Z axis; and ($z_1$, $x_1$) refers to the coordinates of one end of the light barrier 701.

Since the focal length of the parabolic mirror 303 is f as set forth above, the surface equation of the parabolic mirror 303 may be expressed by the following formula (5).

$$X^2 = 4fZ \quad (5)$$

In addition, as shown in FIG. 7, it is possible to draw a straight line passing through an edge point of the catadioptric camera (i.e., the second camera 302) and the focal point of the parabolic mirror 303 so as to define a boundary by which whether the non-fisheye camera can capture the second camera 302 may be distinguished. The straight line stands for a principal ray because it passes through the focal point of the parabolic mirror 303. The intersection of the straight line and the parabolic mirror 303 is the one end of the light barrier 701 whose coordinates are $(z_1, x_1)$. Accordingly, the straight line may be expressed by the following formula (6).

$$X = -\tan\theta Z + z\tan\theta \quad (6)$$

Here, $\theta$ refers of a half view angle when the edge point of the second camera 302 serves as an object point, which may be calculated on the basis of the formulas (3) and (4) above, and z is equal to f.

Thus it is possible to compute the coordinates $(z_1, x_1)$ of the one end of the light barrier 701 on the grounds of the formulas (5) and (6) as follows.

$$z_1 = f + \frac{2f(1 - \sec\theta)}{\tan^2\theta} \quad (7)$$

$$x_1 = -\frac{2f(1 - \sec\theta)}{\tan\theta}$$

Of course, the light barrier 701 shown in FIG. 7 is just an example. It is clear to a person skilled in the art that the shape and location of the light barrier 701 may be changed as long as the light entering the area under the boundary (i.e., the straight line defined by the formula (6) above) may be shielded by the light barrier 701. For instance, the light barrier 701 may not be a curved plate provided on the central part of the front surface of the parabolic mirror 303 as presented in FIG. 7, but is a straight plate disposed between the intersection $(z_1, x_1)$ and its symmetric point with respect to Z axis.

Second Embodiment

A method of shooting light having at least two wavelength bands is given in this embodiment.

Figure 8:
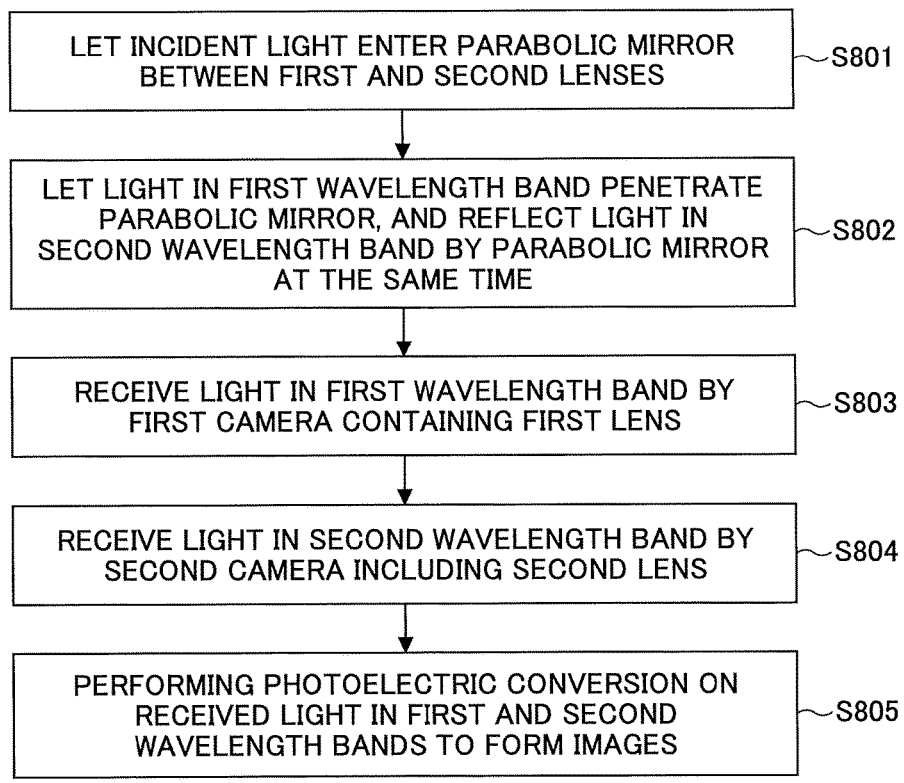
FIG. 8 is a flowchart of a method for shooting light having at least two wavelength bands, according to a second embodiment of the present disclosure.

FIG. 8 is a flowchart of the method according to this embodiment, which is applied to the camera device 300 according to the first embodiment.

As shown in FIG. 8, the method is inclusive of STEPS S801 to S802.

In STEP S801 of FIG. 8, incident light enters the parabolic mirror 303 which is arranged between the first lens of the first camera 301 and the second lens of the second camera 302 as indicated in FIG. 3.

In STEP S802 of FIG. 8, among the incident light, light having a first wavelength band penetrates through the parabolic mirror 303, and at the same time, light having a second wavelength band is reflected by the parabolic mirror 303.

In STEP S803 of FIG. 8, the first camera 301 containing the first lens receives the light having the first wavelength band.

In STEP S804 of FIG. 8, the second camera 302 including the second lens receives the light having the second wavelength band.

In STEP S805 of FIG. 8, photoelectric conversion is conducted in regard to the received light in the first wavelength band and the second wavelength band so as to generate two images, respectively.

Moreover, the method further includes a step (not shown in the drawings) of providing the light barrier 701 on a central part of the front surface of the parabolic mirror 303 so as to shade a part of the curved surface of the parabolic mirror 303 from light, so that the light cannot be reflected by or penetrate through the part of the curved surface of the parabolic mirror 303 to enter the first camera 301 and the second camera 302, as presented in FIG. 7.

Here it should be noted that since the details of the camera device 300 including the first camera 301, the second camera 302, the parabolic mirror 303, and the light barrier 701 have been illustrated in the first embodiment, they are omitted here for the sake of convenience.

Therefore, in the camera device 300 according to the first embodiment and the method according to the second embodiment, by letting the aperture stop of the first camera 301 coincide with the focal point of the parabolic mirror 303, it is possible to achieve the same view field. Furthermore, since the parabolic mirror 303 is set between the first camera 301 and the second camera 302 whose lens are disposed facing each other, the miniaturization of the relating system may be realized. In addition, by further disposing the light barrier 701 on the parabolic mirror 303, it possible to effectively avoid a case where the image of one of the first camera 301 and the second camera 302 exists in the image captured by the other camera.

While the present disclosure is described with reference to the specific embodiments chosen for purpose of illustration, it should be apparent that the present disclosure is not limited to these embodiments, but numerous modifications could be made thereto by a person skilled in the art without departing from the basic concept and technical scope of the present disclosure.

The present application is based on and claims the benefit of priority of Chinese Patent Application No. 201710123684.8 filed on Mar. 3, 2017, the entire contents of which are hereby incorporated by reference.

What is claimed is:

1. A camera device comprising:
   a first camera containing a first lens for receiving light having a first wavelength band;
   a second camera including a second lens for receiving light having a second wavelength band different from the first wavelength band, the second lens being disposed facing the first lens of the first camera; and
   a parabolic mirror set between the first lens and the second lens, able to let the light having the first wavelength band penetrate therethrough, and at the same time, reflect the light having the second wavelength band,
   wherein, the first camera is a non-fisheye camera; the first lens of the first camera is a non-fisheye lens; the second camera and the parabolic mirror form a catadioptric camera; and an aperture stop of the non-fisheye lens coincides with a focal point of the parabolic mirror.

2. The camera device according to claim 1, further comprising:
   a first processor configured to calculate a distance p between the aperture stop of the non-fisheye lens and a central point of a front end of the non-fisheye camera by means of $$\begin{cases} \dfrac{p + l_1}{k} = \dfrac{y_1}{x_1} \\ \dfrac{p + l_2}{k} = \dfrac{y_2}{x_2} \end{cases},$$

and compute a distance s from a vertex of the parabolic mirror to the central point of the front end of the non-fisheye camera by way of s=f−p,
wherein, f is a focal length of the parabolic mirror; $y_1$ is a height of a first object; $y_2$ is a height of a second object; $x_1$ is a height of an image generated from the first object; $x_2$ is a height of an image created from the second object; $l_1$ is a distance from the first object to the central point of the front end of the non-fisheye camera; $l_2$ is a distance between the second object to the central point of the front end of the non-fisheye camera; and k is a distance from an imaging unit in the non-fisheye camera to the aperture stop of the non-fisheye lens.

3. The camera device according to claim 1, further comprising:
a light barrier provided on a central part of a front surface of the parabolic mirror for shading a part of a curved surface of the parabolic mirror from light, so that the light cannot be reflected by or penetrate through the part of the curved surface of the parabolic mirror to enter the first camera and the second camera.

4. The camera device according to claim 3, further comprising:
a second processor configured to determine a size of the light barrier based on $$z_1 = f + \frac{2f(1-\sec\theta)}{\tan^2\theta} \text{ and } x_1 = -\frac{2f(1-\sec\theta)}{\tan\theta},$$

wherein, $z_1$ and $x_1$ are coordinates of one end of the light barrier in a Z-X coordinate system whose origin is located at a vertex of the parabolic mirror, Z axis is a common optical axis of the catadioptric camera and the non-fisheye camera, and X axis is perpendicular to Z axis; f is a focal length of the parabolic mirror; and θ is a half view angle corresponding to an edge point of the second camera.

5. The camera device according to claim 1, wherein, the catadioptric camera is an object side telecentric optical system.

6. The camera device according to claim 1, wherein, the light having the first wavelength band is visible light, and the light having the second wavelength band includes one of near-infrared light, short-wave infrared light, mid-wave infrared light, and long-wave infrared light; or
the light having the second wavelength band is visible light, and the light having the first wavelength band includes one of near-infrared light, short-wave infrared light, mid-wave infrared light, and long-wave infrared light.

7. A method of shooting light having at least two wavelength bands, comprising:
receiving incident light by a parabolic mirror arranged between a first lens and a second lens disposed facing each other;
reflecting light having a second wavelength band by the parabolic mirror, light having a first wavelength band different from the second wavelength band penetrating through the parabolic mirror at the same time;
receiving the light having the first wavelength band by a first camera containing the first lens able to receive the light having the first wavelength band;
receiving the light having the' second wavelength band by a second camera including the second lens able to receive the light having the second wavelength band; and
performing photoelectric conversion on the received light having the first wavelength band and the received light having the second wavelength band so as to form two images, respectively,
wherein, the first camera is a non-fisheye camera; the first lens of the first camera is a non-fisheye lens; the second camera and the parabolic mirror form a catadioptric camera; and an aperture stop of the non-fisheye lens coincides with a focal point of the parabolic mirror.

8. The method according to claim 7, before the letting incident light enter a parabolic mirror arranged between a first lens and a second lens disposed facing each other, further comprising:
calculating a distance p between the aperture stop of the non-fisheye lens and a central point of a front end of the non-fisheye camera by means of $$\begin{cases} \frac{p+l_1}{k} = \frac{y_1}{x_1} \\ \frac{p+l_2}{k} = \frac{y_2}{x_2} \end{cases},$$

and computing a distance s from a vertex of the parabolic mirror to the central point of the front end of the non-fisheye camera by way of s=f−p,
wherein, f is a focal length of the parabolic mirror; $y_1$ is a height of a first object; $y_2$ is a height of a second object; $x_1$ is a height of an image generated from the first object; $x_2$ is a height of an image created from the second object; $l_1$ is a distance from the first object to the central point of the front end of the non-fisheye camera; $l_2$ is a distance between the second object to the central point of the front end of the non-fisheye camera; and k is a distance from an imaging unit in the non-fisheye camera to the aperture stop of the non-fisheye lens.

9. The method according to claim 7, further comprising:
providing a light barrier on a central part of a front surface of the parabolic mirror for shading a part of a curved surface of the parabolic mirror from light, so that the light cannot be reflected by or penetrate through the part of the curved surface of the parabolic mirror to enter the first camera and the second camera.

10. The method according to claim 9, further comprising:
determining a size of the light barrier based on $$z_1 = f + \frac{2f(1-\sec\theta)}{\tan^2\theta} \text{ and } x_1 = -\frac{2f(1-\sec\theta)}{\tan\theta},$$

wherein, $z_1$ and $x_1$ are coordinates of one end of the light barrier in a Z-X coordinate system whose origin is located at a vertex of the parabolic mirror, Z axis is a common optical axis of the catadioptric camera and the non-fisheye camera, and X axis is perpendicular to Z axis; f is a focal length of the parabolic mirror; and θ is a half view angle corresponding to an edge point of the second camera.

* * * * *